United States Patent [19]

Feng et al.

[11] Patent Number: 5,147,786

[45] Date of Patent: Sep. 15, 1992

[54] IMMUNOASSAY FOR THE DETECTION OF α-HALOACETAMIDES

[75] Inventors: Paul Feng, Babler; Stephen J. Wratten, Maryland Heights; Peggy A. Winzenburger, High Ridge; Cindy J. Gross, St. Louis; Dennis K. Flaherty, Ballwin, all of Mo.

[73] Assignee: Monsanto Company, St. Louis, Mo.

[21] Appl. No.: 619,560

[22] Filed: Nov. 29, 1990

Related U.S. Application Data

[63] Continuation of Ser. No. 184,854, Apr. 22, 1988, abandoned.

[51] Int. Cl.$^5$ .................... G01N 33/552; C07K 17/14
[52] U.S. Cl. .................... 435/7.94; 435/975; 530/389.8; 530/404; 530/807
[58] Field of Search ............ 435/7.5, 7.72, 7.94, 435/961, 975; 436/528, 532, 533, 538, 541, 543, 547, 815, 824, 540; 530/387, 404, 413, 806, 807

[56] References Cited

U.S. PATENT DOCUMENTS 4,021,224  5/1977  Pallos et al. .................... 564/210 X
4,530,786  7/1985  Dunbar et al. .................. 436/815 X

OTHER PUBLICATIONS

Huber et al, "Solid-Phase Enzyme Immunoassay . . . ", Chemical Abstract 104, p. 370, #115681f (1986).
Schwalbe et al, "Enzyme Immunoassay and Fluoroassay for Herbicide . . . ", Chemical Abstracts 101, p. 195, #49997y (1984).
Kelley et al, "Chlorsulfuron Determination in Soil Extracts . . . ", Chemical Abstracts 103, p. 262, #155689a, (1985).

*Primary Examiner*—Mary E. Ceperley
*Attorney, Agent, or Firm*—William I. Andress

[57] ABSTRACT

The disclosure herein relates to antigens, antibodies, antisera and diagnostic assay kits used in an enzyme-linked immunosorbent assay (ELISA) for α-haloacetamide herbicides.

20 Claims, No Drawings

IMMUNOASSAY FOR THE DETECTION OF α-HALOACETAMIDES

This is a CONTINUATION of application Ser. No. 07/184,854, filed Apr. 22, 1988, now abandoned.

BACKGROUND OF THE INVENTION

The invention herein relates to the field of immunochemical assays of pesticides. In particular the specific method described and claimed relates to an enzyme-linked immunosorbent assay ("ELISA") for the detection of α-haloacetamides.

Immunoassays are rapidly becoming an important technique in the analysis of pesticide residues. As used herein the term "pesticides" refer to chemicals used to control weeds or animal pests in agricultural crops.

Basic immunoassay techniques in use today for detecting pesticides or analytes, include those called the "sandwich", "labeled analyte" and "second antibody", e.g., enzyme-linked immunosorbent assay ("ELISA") methods. A modification of the labeled analyte method is known as an enzyme multiplied immuno technique ("EMIT"). The methods will be described in more detail below.

In any immunoassay, the antibodies are the essential reagent which provides the specificity and dictate the ultimate level of sensitivity which can be achieved. Antibodies are immunoglobulin protein molecules produced as part of the mammalian immunodefense system. Gamma-immunoglobulins (IgG), which are the antibody proteins most frequently used in immunoassays, have molecular weights of about 160,000 and consist of two variable binding regions per molecule and a nonbinding region with a constant amino acid sequence which is characteristic for each animal species. These proteins are normally found in the blood and lymph systems of mammals and are commonly obtained from a blood sample by removal of the blood cells by clotting or centrifugation. The resulting preparation is the serum, which is often called "antiserum" or "immune serum" when it contains antibodies of interest. Such an antiserum contains a mixed population of many antibodies, some of which are directed toward the analyte of interest but most of which have resulted from other foreign substances to which the animal has been exposed. Because of this heterogeneous nature, antisera are also often called polyclonal antibodies.

Nearly all of the pesticide immunoassays described in the literature have employed rabbit antisera as their source of antibodies, at least in the initial stages. Since the population of antibodies in an animal's blood can vary over time, a single sample obtained from one bleeding or by pooling several bleedings is usually used throughout the experimental period. Other animals such as mice, goats or horses can be used to supply antibodies, but rabbits are particularly easy to keep and work with. Most investigators have simply used diluted antisera in their assays, although some have purified the immunoglobulins by precipitation or immunoaffinity columns. The major advantages of using purified antibodies are realized if there is an unwanted antibody population in the antiserum which leads to unacceptable interferences, although increased sensitivity can also be realized in some assay formats. If the investigator wants to covalently link a label or tracer to the antibody for use in a sandwich assay as described below it is also essential to purify the antibody first. Using modern methodology, antisera can often be diluted 1:1000 or more with buffer prior to their use in immunoassays, allowing many assays to be completed with a single blood sample.

In some studies in the literature, monoclonal antibodies are employed. These antibodies are obtained from the medium fluids of hybridoma cell lines or from ascites tumors produced in mice intentionally immunized with an appropriate hybridoma. The hybridoma cell lines are produced by a lengthy procedure initiated from spleen cells of mice which have been previously induced to produce the desired antibodies in the same way as the rabbits. The sequence of operations required to produce and identify useful monoclonal antibodies must be performed by someone with prior experience, since many specialized tasks and equipment are necessary. Such a process is best reserved for those cases where promising antisera have already undergone preliminary study and a clear intention to utilize the resulting hybridomas has been established. Such monoclonal antibodies are advantageous because a single homogeneous immunoglobulin is produced which may have a very narrow, well-defined specificity, which will be invariant from batch to batch, and which can be made available in large quantities. These characteristics make monoclonal antibodies particularly attractive for the production of diagnostic kits.

Because of their low molecular weight, there is a problem in the production of antibodies directed against pesticides. Unlike larger molecules, low molecular weight pesticide analytes, must be conjugated to a carrier protein, prior to immunizing the animals, because the free pesticide itself is too small to elicit antibody production even though it can bind to the antibodies once they are formed. This trait defines the pesticide as a "hapten" in immunological terms. The pesticide moiety should be covalently attached to the carrier; usually proteins such as bovine serum albumin (BSA), ovalbumin (OA), human serum albumin (HSA), or keyhole limpet hemocyanin (KLH) are used as carriers. The extent to which the hapten, after conjugation to the protein, resembles the free pesticide spatially and electronically will influence the specificity and sensitivity of the assay. The choice of protein carrier may be influenced by the projected use of the assay; for example, HSA should not be used if the assay will be used for analysis of human serum samples.

A careful strategy must be developed to design the hapten conjugate to achieve the desired assay specificity. In general, the portions of the hapten molecule which are more distant from the point of attachment to the protein carrier will have more influence on the antibody specificity than those used to accomplish the linkage. Formation of an amide bond to pendant lysine amino groups on the protein using carbodiimide reagents or other types of carboxyl activation have most commonly been used to attach the hapten, although nearly any kind of stable covalent linkage can be used. Often analogs or metabolites of the target pesticide with chemical functionality amenable to linkage formation are very useful. In addition, a spacer molecule which is commonly two to six carbon atoms long may be incorporated between the hapten and the carrier. Some investigators carefully determine the number of haptens attached to each molecule of carrier, which can best be determined using radiolabeled haptens or less accurately by UV absorbance, but others simply immunize the animals to determine if the conjugation reaction was successful. Although there is no clear agreement as to the ideal number of haptens per molecule of carrier, many investigators seem to target a ratio of one hapten for each 5000 to 20,000 daltons of protein molecular weight. As the prior discussion suggests, there are no rules for conjugate preparation, and several possible approaches should be considered or even attempted simultaneously. It is often useful to prepare conjugates using more than one carrier since subsequent steps will require the use of a second hapten conjugate to eliminate responses from antibodies directed toward the protein carrier rather than the hapten; a positive reaction with different proteins bearing the same hapten is good preliminary evidence that the antibodies may have desirable properties. In addition, if it becomes worthwhile to purify the antibodies using affinity columns, a second conjugate will be useful.

Animals are usually immunized subcutaneously at several sites initially with about one milligram of the hapten conjugate ("immunogen" or "antigen") per kilogram of body weight in Freund's complete adjuvant. This preparation contains heat-killed bacteria which enhance the animal's immune response. Subsequent booster immunizations are usually made on a regular schedule using about 20% of the original immunogen in Freund's incomplete adjuvant. Blood is then withdrawn from the animals at a fixed period of time, such as ten days after each boost, commencing four to eight weeks after the initial injection.

A second type of antibody is sometimes mentioned in the literature as part of the assay strategy. As discussed below, most assay techniques require a step in which the analyte-antibody complex must be physically separated from the rest of the mixture. One convenient approach is to use a second antibody from a different animal species which has been developed against the invariant part of the original (for example, rabbit) immunoglobulin. Such "second antibodies" are commonly called "goat-anti-rabbit" or GAR, for example, and are commercially available from immunological suppliers, often with convenient tracer molecules already covalently bound to them.

Once the antibodies have been obtained from the animal source, they must be evaluated for applicability toward analysis of the pesticide of interest. The formation of a complex through non-covalent binding of the antibody to the pesticide, much like the binding of an enzyme to its substrate, is of prime importance in the immunoasssay. All other phases of the process are designed to detect and quantitate the extent of formation of this complex. A variety of approaches has been devised toward this end.

In the early 1980's, solid phase immunoassay techniques were developed and have replaced older methods in nearly all assay protocols. Accordingly, the discussion below will be with reference to these solid phase techniques only.

Solid phase techniques rely on the adsorption of protein-hapten conjugates onto polystyrene or latex surfaces at high pH's. This non-covalent binding is essentially irreversible during the assay, and serves to immobilize a chosen protein without altering its immunological interactions. Although many geometric possibilities exist, by far most laboratory assays are performed in 96-well polystyrene "microtiter" plates which are available from many suppliers. After the desired conjugate is bound or "coated" onto the surface of each small well, the remaining binding sites are blocked using an inert protein such as gelatin or BSA. Although the binding capabilities of different plates vary, the availability of 96 wells on each plate combined with many types of automated liquid dispensing equipment allows the inclusion of standards in each analysis plate to overcome this problem. The immobilized conjugate can then be exposed to a series of reagent solutions, which are discarded after each step, separating those molecules which bind to the immobilized protein from all the rest. In addition, the capacity of each well is 200-300 microliters, so that the assay has been miniaturized as well as simplified. These improvements combined with the standardization of microtiter plate geometry has allowed the manufacture of equipment to process all 96 wells in such a plate simultaneously. With these features, quadruplicate analyses, for example, of many tens of samples can be done quickly using less than one milliliter of each sample.

There are three basic strategies used in modern immunoassays, only two of which appear applicable to pesticide analysis. These can be referred to as "sandwich", "labeled-analyte", and "second-antibody" methods. An essential part of each is the generation of calibration curves using known amounts of the desired analyte. The "sandwich" approach requires two antibodies which both recognize the analyte; both may actually be the same protein, one sample of which has been linked to a tracer molecule. The sandwich approach is attractive because the signal which develops in the sample wells at the assay's completion is directly proportional to the amount of analyte present and it does not rely on a competitive binding reaction. Unfortunately, it is not viewed as spatially possible to have two antibody molecules bound to a single small pesticide molecule simultaneously; thus, the sandwich technique is not applicable to pesticide analysis.

The "labeled-analyte" method is a conceptually simpler method than the second-antibody approach, and it is almost always used with radioimmunoassays (RIA). It requires that a sample of the pesticide be radiolabeled or covalently attached to an enzyme or fluorescent tracer. A constant known amount of this labeled pesticide is allowed to compete with the free pesticide in the unknown sample for the limited number of antibody binding sites attached to the well's surface. After washing away the unbound pesticide, both labeled and unlabeled, the amount of label remaining in the well is inversely proportional to the amount of pesticide originally in the unknown sample. In principle, the labeled analyte can have a slightly different structure than the measured analyte as long as the two molecules compete for the same binding site and the presence of the actual analyte inhibits the binding of the label in the concentration range of interest. This strategy has been used in the case of PCB's where many similar structures are of simultaneous analytical interest. The three most common types of labeled analyte involve radioactivity or the preparation of covalent conjugates of the analyte with fluorescent tags or enzymes.

The "second-antibody" method is commonly used in enzyme assays (EIA) such as the enzyme-linked immunosorbent assay (ELISA), because the required second antibodies, covalently labeled with an enzyme, are commercially available. In this approach, a protein conjugate of the pesticide using a different protein than that employed as the original immunogen, is coated onto the well's surface (called the "coating" or "screening" antigen). The fixed amount of hapten moieties on this coating antigen then compete with the free pesticide molecules in the unknown sample for the limited number of antibody binding sites. The interaction between the antibody and pesticide in the fluid phase inhibits the ability of the antibody to bind to the solid phase coating or screening antigen. Hence, when high concentrations of pesticide are present in the test sample, small concentrations of antibody will react with the solid phase coating antigen. Conversely, high concentration of antibodies will be bound to the solid phase when low levels of pesticides are present in the test sample. The antibodies bound to the solid phase are then detected by formation of another complex using a commercially available labeled second antibody directed toward the heavy chain constant portion of the pesticide-specific antibody. After washing out the unbound labeled second antibody, the label remaining in each well is inversely proportional to the amount of pesticide in the unknown sample.

In all immunoassay techniques, a final measurement must be made which can be correlated using a calibration curve to the amount of pesticide present in the unknown sample. The type of measurement will depend upon the nature of the label which was attached to the hapten, antibody, or second antibody in the assay strategy. Radioimmunoassay techniques were the most common assays in use a few years ago, and are still in wide use today. Although $^{14}C$-labeled samples of pesticides are usually available, the specific activities of these compounds cannot often be made high enough to allow accurate detection of picogram to nanogram amounts of pesticide. Since most pesticide immunoassays are competitive binding assays, the detection limit of the assay will depend directly upon the mass of labeled compound which is competing with the unknown sample, and therefore on the specific activity of the radiolabel. For this reason, tritium or $^{125}I$ radiolabels are required to produce very sensitive immunoassays. The synthesis, purification, use, and disposal of such high specific activity radiolabels may often be a major hurdle standing in the way of utilization of radioimmunoassays for pesticide analysis in many laboratories.

An attractive alternative is the use of enzyme-labeled components in the immunoassay strategy. The quantitative measurement of the amount of enzyme present at the final stage of the assay is based upon the addition of an excess of a substrate which the enzyme can convert to an easily quantifiable product. Most often this has involved formation of a colored product via the action of the enzyme on a substrate without these properties. Typical examples include alkaline phosphatase/p-nitrophenyl phosphate or horseradish peroxidase/o-phenylenediamine combinations, although nearly any rapid enzyme/substrate reaction which produces a stable, easily quantified product could be used. The above two enzymes are commonly employed because they have high activity and can be covalently bound to a variety of "second antibodies" by simple chemical techniques. Galactose conjugates of fluorescent phenols such as β-napthol or 4-methylumbelliferone can also be used in conjunction with a β-galactosidase label to generate a fluorescent signal which is proportional to the enzyme concentration. In general, the colored products produced by horseradish peroxidase or alkaline phosphatase seem to be most conveniently measured by common laboratory equipment unless the sample matrix generates a competing signal. Certainly for use in field test kits, a visible signal which does not require complex equipment to detect a positive sample is preferable. In some cases, an additional non-covalent binding step has been used with enzyme labels which involves the tight binding between biotin (vitamin H) and avidin, a biotin-binding protein from egg whites. In this strategy, for example, biotin-labeled second antibodies are mixed with avidin-enzyme conjugates, usually to achieve an additional amplification of the ultimate enzyme signal. This strategy has not been specifically reported for pesticide analysis.

The third type of label which is sometimes used is a fluorescent label, which is distinguished from an enzyme label acting on a fluorescent substrate. In this case, the hapten or second antibody is covalently linked directly to the fluorophore, for example fluorescein. The fluorescent label can then function just like a radiolabel except that the final measurement involves the excitation and emission process. The fluorescent approach offers the potential advantage of increased sensitivity or diminished background signal when interferences are a problem without the need of radioactivity. The equipment for measuring fluorescence is not quite as commonly available as those for colorimetric determinations using enzyme labels. One adaptation which has been advocated in some pesticide analyses, apparently mainly as a proprietary foothold for kit development, is the fluorescence polarization technique. In this method, the optical rotation of the fluorescent emission from a polarized excitation beam is correlated to the degree of antibody-pesticide complex formed. It has not seen wide usage.

There is one other approach which is very attractive for pesticide immunoassays which involves a proprietary strategy developed by one company for application in clinical diagnostics. The method is called EMIT (Enzyme Multiplied Immuno Technique) and is a modification of the labeled-analyte approach. The analyte must be covalently conjugated to an enzyme label close to the active site of the enzyme so that complexing to the antibody spatially inhibits the enzyme reaction. When this hapten-enzyme conjugate is incubated with the test sample and the antibody in a homogeneous solution, no physical separation of the bound and unbound moieties is required because only those haptenenzyme conjugates which are unbound can be detected when the substrate is added. Therefore, only those samples which contain the pesticide will develop a detectable enzyme product since the presence of the free pesticide is required to prevent the inhibitory binding of the antibody to the enzyme-hapten conjugate.

Immunoassays inherently offer an extremely sensitive technique in relation to the amount of effort which must be expended. In most of the pesticide immunoassays, small aliquots of water, urine, serum, or extract samples can be used directly in the assay without further cleanup or concentration. This is in obvious contrast to many other instrumental methods where often tens or even hundreds of milliliters of a sample may have to be extracted, fractionated, and concentrated prior to the final analytical step. Using the direct immunoassay analysis format, the typical sensitivities reported for pesticide immunoassays have detection limits in the range 1–10 nanograms per milliliter (PPB) give or take one order of magnitude. These sensitivities are usually more than adequate for most pesticide analyses; obviously these levels could be lowered even further by applying the extraction and concentration procedures which have likely already been developed for most instrumental pesticide methods prior to the actual immunoassay step, although much of the potential time savings would then be sacrificed.

The working dynamic range for most immunoassays seems to span about two orders of magnitude, such as 1-100 parts per billion (PPB). When analysis of samples above the appropriate concentration range is attempted, most of the binding sites are already occupied, and the change in signal produced by the additional amounts of pesticide is undetectable. In many cases, the optimized immunoassay may actually be too sensitive for convenient direct assay of some pesticide samples, requiring that they be diluted prior to analysis or that the assay protocol be modified by increasing the number of total binding sites available, effectively reducing overall sensitivity. These problems are the direct result of the competitive binding nature of the assay format, and are inherent in the immunoassay strategy. For situations in which samples are expected to contain pesticide at concentrations spanning several orders of magnitude, a tiered approach may be useful in which several immunoassays are used to "sort" the samples into the most appropriate assay to achieve optimum precision. This can be accomplished readily because immunoassays lend themselves to automation very well so that doubling or even increasing the sample load by a factor of five will not overtax the system once all of the other details are worked out.

In general, immunoassays are very selective for the analyte of interest, which is the basis for their direct application to crude unpurified samples. Often this selectivity is evaluated in the literature by reference to a table of cross reactivities. This concept compares the intensity of the signal produced in the assay by a fixed amount of each of a group of compounds which might conceivably interfere. The amount is usually the amount of the desired analyte which produced about a 50% response. The intensity of the signal produced by the other compounds as compared to that of the desired analyte can then be expressed as "% cross reactivity". Alternatively, the same concept can be expressed by citing the concentration of each compound required to produce a 50% response in the assay, called IC$_{50}$. The extent of cross reactivities of analogous compounds cannot be predicted. Immunoassays are capable of distinguishing one optical enantiomer from the other if such isomerism exists. In some cases, the similarity of other commercial compounds can present a substantial problem to use of the immunoassay, while in other cases the response of other analogs can be beneficial, particularly if analysis of metabolites or a group of similar compounds is desired. Generally, purification of polyclonal antibodies via affinity columns can be used to remove undesirable cross-reacting populations; the ultimate step in this approach is the use of a single monoclonal antibody which has been selected to have exactly the desired specificity.

Although a substantial number of immunoassays have been reported in the literature for pesticides and environmental contaminants, only those which can detect parathion, paraoxon, or paraquat in human serum as a result of poisoning appear to have been actually used extensively. A number of reasons can be suggested. Most of the compounds tested have not enjoyed great commercial success during the period for which the immunoassay has been available, suggesting that the desire for great numbers of analyses may not have materialized. The environmental contaminants such as DDT, PCB's, kepone, etc. have traditionally been measured using gas chromatography, which allows simultaneous detection of most of the compounds of concern in a single analysis. In this respect, the selectivity of an immunoassay is actually a disadvantage, and should be considered as one criterion in the decision regarding choice of potential analytical methodology. Immunoassays are advantageous from a time and sample-size standpoint, and the impact of these advantages multiplies as the number of required assays increases. The time required to develop an immunoassay to a usable stage is clearly greater than to develop a comparable instrumental method. Even though an immunoassay method may have been published, establishing it as a useful technique in another laboratory will require a substantial time investment. In addition, before the advent of enzyme (ELISA) or other kinds of labels, the requirement for use of radioisotopes almost certainly limited the utility of immunoassays.

Of the various other pesticides which have been analyzed by immunological methods, there are mentioned atrazine, chlorosulfuron, cyanazine, 2,4-D, diclofopmethyl, pentachlorophenol, 2,4,5-T and terbutryn. To our knowledge no immunoassay for α-haloacetamide herbicides has been described in the literature prior to this invention. And to our knowledge, only one literature reference even mentioned any α-haloacetanilides (viz. alachlor, metolachlor and propachlor) as cross-interferants in an immunoassay system, i.e., one designed to detect the fungicide metalaxyl. That system is described in an article by W. H. Newsome, J. Agric. Food Chem. 1985, 33, 528–530.

Accordingly, it is an object of this invention to provide an ELISA immunoassay system which provides novel antigens for raising novel antibodies in novel antisera for detecting α-haloacetamides, particularly α-chloroacetanilides, best exemplified by the commercial products alachlor, allidochlor, amidochlor, butachlor, metazalachlor, metolachlor, pretilachlor and propachlor.

SUMMARY OF THE INVENTION

It has been found that the above and other objects of the present invention are obtained by an ELISA immunoassay system designed to provide an antigen (or as used synonymously herein conjugate) comprising an α-haloacetamide hapten covalently-bound to a macromolecular carrier; immunizing the host animal, preferably rabbits, in which antibodies specific to said hapten are raised; extracting from said host an antisera from which the antibodies are obtained and used to detect said hapten in a solid phase analysis system using a second antibody inhibition means, e.g., goat anti-rabbit gamma-globulin conjugated to horseradish peroxidase, and measuring the presence or concentration of the hapten against standard colorimetric calibration curves.

α-Haloacetamides useful for preparing antigens with proteins and against which antibodies are raised are those having the formula

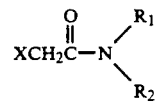

wherein X is a halogen;

$R_1$ and $R_2$ are independently radicals having up to 8 carbon atoms which are alkyl, alkenyl, alkynyl, alkoxyalkyl, polyalkoxyalkyl, acyl or acylamidomethyl; aryl or arylalkyl radicals having up to 10 carbon atoms; heterocyclyl or heterocyclylmethyl radicals having up to 10 ring atoms of which 1-3 may be nitrogen, oxygen and/or sulfur atoms; or any of said radicals substituted with one or more alkyl, haloalkyl, alkenyl, haloalkenyl, or alkoxyradicals having up to 5 carbon atoms, halogen, nitro or cyano group.

α-Chloroacetanilides of particular interest are those having the formula

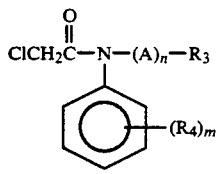

wherein A is a $C_{1-4}$ straight or branched-chain alkylenyl radical and n is zero or 1; $R_3$ is hydrogen, $C_{1-5}$ alkyl or haloalkyl; $C_{1-6}$ acyl or acylamido; a heterocycyl or heterocyclylmethyl radical having up to 10 ring atoms of which 1-3 may be nitrogen, oxygen and/or sulfur, optionally substituted with $C_{1-5}$ alkyl or alkoxy radicals; or an —$OR_5$ radical where $R_5$ is a $C_{1-6}$ alkyl, haloalkyl or alkoxyalkyl radical, and $R_4$ is a $R_5$ radical, $CF_3$, $NO_2$ or an alkoxy radical having up to 5 carbon atoms and m is 0-5.

Preferred macromolecular carriers are serum proteins such as human serum albumin (HSA), ovalbumin (OA), bovine serum albumin (BSA), sheep gamma-immunoglobulin (IgG), or keyhole limpet hemocyanin. A carrier protein which could be present in the sample matrix should be avoided, e.g., ovalbumin conjugates would not be appropriate immunogens for an analysis targeted toward egg whites.

Preferred means for covalently linking the hapten to the protein carrier to form the conjugate (antigen) thereof are the use of sulfhydryl groups introduced onto the lysine residues of the proteins with compounds such as N-acetyl homocysteine thiolactone (AHT) or S-acetylmercaptosuccinic anhydride (AMSA). An important feature of the use of sulfhydryl binding of the hapten to the protein is the displacement of the α-halogen by a thiol moiety to produce the corresponding thioether. Such binding has resulted in greater specificity and reduced cross reactivity of antibodies for the hapten with compounds of related structure.

The covalently-bound hapten-protein antigen of this invention is represented by the formula

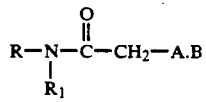

wherein R and $R_1$ are as defined above for the α-haloacetamide;
A is the residue of a thiolating agent, and
B is a serum protein covalently bound to A.

Exemplary and preferred antigen structures are those wherein in the above formula B is BSA or IgG and A is one of the thioether groups.

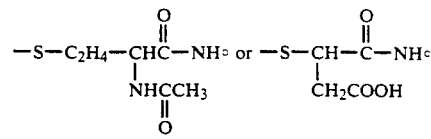

More preferred hapten-protein antigens are those α-chloroacetanilides of particular interest according to the above formula wherein R is the —$(A)_n$—$R_3$ radical and $R_1$ is a phenyl or substituted phenyl radical.

A particularly preferred class of hapten-protein antigens are those according to the above formula wherein B is BSA or IgG, A is the thioether residue derived from AHT or AMSA and the hapten is derived from the above mentioned commercial α-chloroacetanilide herbicides.

Still more preferred hapten-protein antigens are those depicted graphically in Example 1 below.

Another aspect of this invention relates to immunoassay diagnostic kits which may be used in the field for on-the-spot analysis of samples to determine the presence and amount of any α-haloacetamides which may be present.

DETAILED DESCRIPTION OF THE INVENTION

The immunoassay system for α-haloacetamides provided by this invention will be exemplified in Example 1 having reference to the most preferred embodiment for detecting an α-chloroacetanilide, i.e., alachlor (α-chloro-2',6'-diethyl-N-methoxymethyl acetanilide), the leading commercial preemergence herbicide against grasses and some broadleaf weeds in corn and soybeans. All reagents used in the assay are commercially available and/or obtained by known procedures.

Example 1

Conjugate Preparation. Hapten (alachlor $^{14}$C-labeled) was covalently attached to BSA and IgG. Sulfhydryl groups, introduced onto the lysine residues of the proteins with AHT and AMSA, were reacted with the hapten to produce thioether bonds through the displacement of the hapten-chlorine atom by the thiol moiety according to the following equation, having reference to alachlor, (structural formulae for the conjugates are deduced);

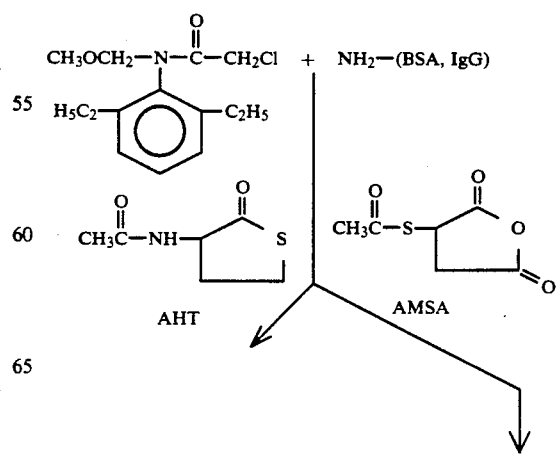

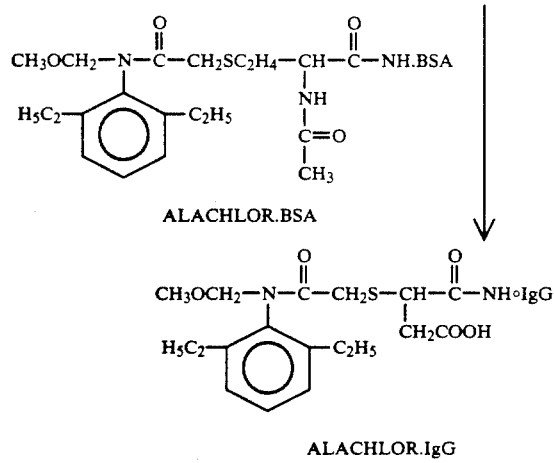

ALACHLOR.BSA

ALACHLOR.IgG

The protein (200 mg BSA or IgG) and 25 equivalents of AHT or AMSA were dissolved in water (6 mL) at 0° C., to which the hapten (25 equivalents) dissolved in dioxane (1 mL) was slowly added. Carbonate buffer (1 M, pH 11) was then added to adjust the pH to 11 and reaction mixture stirred at 0° C. for 15 min. Following 2 hrs of stirring at 22°-50° C., the reaction mixture was neutralized and the hapten-protein conjugate was purified by a 24 hour dialysis against running-water or by Sephadex G-25 size exclusion chromatography (2×50 cm column using 0.2 M NaCl). Both methods effectively separated the hapten-protein conjugates from the excess hapten and thiolating agents. The radioactivity of each hapten-protein conjugate was determined by liquid scintillation counting; the protein concentration for BSA and IgG were calculated from the UV absorbances at 280 nm and their molar extinction coefficients (39 and 188 mM/cm for BSA and IgG, respectively). Calculations showed that 12 and 19 moles of alachlor per mole of BSA and IgG, had been conjugated to the proteins. The IgG conjugate was used in the immunization of the rabbits and the BSA conjugate was used in the screening of the antisera. The hapten-protein conjugates were lyophilized and stored at −20° C.

Antibody/Antiserum Generation. The IgG conjugate of alachlor (1 mg in 0.3 mL of PBS) was emulsified with Freund's complete adjuvant (1 mL), and then was injected intradermally into female New Zealand white rabbits. The animals were boosted at 4-6 week intervals with 0.1 to 0.5 mg of the same immunogen in Freund's incomplete adjuvant. Whole blood (25 mL) was obtained 1-2 weeks after each boost through the ear vein, allowed to coagulate overnight at 4° C., and centrifuged to generate the serum. Aliquots of the sera were stored in small vials at −20° C. The alachlor-IgG conjugate was also used by us to immunize mice for the production of monoclonal antibodies.

Immunoassays. A known "checkerboard assay" was initially conducted with each serum sample after the first boost to detect the production of antibodies against alachlor. The alachlor-BSA conjugate (512 ng/0.1 mL) in carbonate buffer (0.05 mM, pH 9.6), was serially diluted (one to two) down to 4 ng/0.1 mL with the same buffer. On a 96-well microtiter plate (8 horizontal rows ×12 columns of wells), 0.1 mL (512 ng/0.1 mL) of the screening antigen solutions were pipetted into all 12 wells of the first row. The next 7 rows received the subsequent dilutions of the screening antigen. The plate was covered with Parafilm and stored overnight at 4° C. The next morning, the unbound screening antigen was removed from the wells by washing three times with phosphate buffered saline solution (0.01 M phosphate buffer of pH 7.4, 0.15 M NaCl; PBS). The remaining active sites in the wells were blocked with PBS-8% non-fat dry milk solution, (NFDM, 0.3 mL) for 1 hr at 22° C. Serum, which had been stored at −20° C., was freshly thawed and serially diluted (one to two) from 1,000 to 64,000-fold using PBS-T (PBS containing 0.02% Tween 20). Starting with the most concentrated solution, 0.1 mL of the serum solution was pipetted into all 8 wells of column 1; the remaining columns received the subsequent dilutions of the serum solution. The plate was covered and incubated at 22° C. for 1.5 hrs. Following triplicate washes of the wells with PBS-T, each of the wells received 0.1 mL of goat antirabbit gammaglobulin conjugated to horseradish peroxidase (GAR-HRP) freshly thawed and diluted 4,000 fold with PBS-1% NFDM. After a final wash cycle (4 times) with PBS-T, freshly prepared 0-phenylene diamine (PDA) substrate solution (0.2 mL, 0.04 mg/mL PDA and 0.01% $H_2O_2$ in 0.05 M citric acid and 0.15 M sodium dibasic phosphate, pH 5.0) was dispensed into each of the wells and incubated in the dark at 22° C. for 30-60 min. Sulfuric acid (4 N, 50 μL) was added to each of the wells to stop the reaction, and the final absorbances of the wells (490 nm) were recorded. The presence of antibodies in the serum which recognized the screening antigen produced a gradient of absorbances dependent on the screening antigen and serum concentrations in the wells.

These checkerboard assays demonstrated the presence of antibodies in the sera which recognized the alachlor-BSA conjugate, and established the most sensitive feasible combination of serum and screening antigen concentrations to be used in subsequent assays. For alachlor, this was established at 5 ng/well of the screening antigen and a 3,500-fold dilution of the serum from the seventh bleed. Plates coated with the screening antigen were stored desiccated at −20° C. and remained stable after 4 months.

The inhibition ELISA required one additional step in the assay procedure described above. Equal volumes of the diluted serum and aqueous alachlor standard or unknown sample were mixed and preincubated at 22° C. for 1 hr. This mixture (0.1 mL/well) was then analyzed in 6 replicate wells on the plate. The presence of free alachlor inhibited the binding of the antibody to the alachlor-BSA conjugate, resulting in an inhibition of the development of absorbance at 490 nm. The amount of free alachlor was indirectly proportional to the intensity of color developed. Levels of alachlor in unknown water samples were calculated based on the alachlor standards on the same plate. Alachlor standards (0, 0.2, 0.5, 1.0, 3.0, 5.0, and 35 8.0 ppb in deionized water) were stored at −20° C. in 1-mL portions, and were freshly thawed for each assay.

Data Calculations. The lay-out of a typical 96-well microtiter plate is 8 rows of 12 columns in an inhibition ELISA assay for alachlor. The first 6 wells in the first column of wells were not coated with the screening antigen and served as the background wells. The first 6 wells in the remaining 7 columns of wells were reserved for the seven alachlor standards (0 to 8 ppb) listed above. The remaining wells in all 8 rows were used for the samples. The uncorrected absorbances of the wells determined by the Bio-tek reader were used in the following calculations. The median was calculated for the 6 replicate background wells and was then subtracted from the medians of the standards and samples. All the median values were divided by the median of the standard without alachlor (0 ppb) to generate percentages of absorbances. The percent absorbance of the alachlor standards was then plotted on the Y axis against the logarithm (base 10) of the actual concentrations of alachlor on the X axis. A hyperbolic curve was drawn through the standards, and the resulting standard curve was used to calculate the concentrations of alachlor in the unknown samples.

The calculations described above were usually carried out using a computer program. The absorbances from the Bio-tek reader were transferred directly into a Digital-Vax computer file, which was then processed by an RSl program. The logit values for the % absorbances were calculated (logit % absorbance $= \ln$ [% absorbance/[100 $-$ % absorbance]]) and plotted on the y axis against the logarithm (natural) of alachlor concentrations in ppb. The logit function served to partially linearize the data, producing a line through the standard points. The logit value for each sample was then calculated based on the equation of the line to determine the concentration of alachlor in the sample.

Cross-Reactivity Studies. The reactivity of the antibodies with a series of alachlor analogs was compared to that of alachlor. The concentration of a molecule producing a 50% inhibition in absorbance in the inhibition ELISA was defined as its $IC_{50}$ value (50% inhibition concentration). The $IC_{50}$ value of alachlor (picomoles per mL) was divided by the corresponding value from the cross reactive analog and multiplied by 100 to produce the percent cross-reactivity values.

Affinity Chromatography. The preparation of affinity columns using rabbit antisera was as follows: The rabbit IgG's were purified by passing 5 mL of the antiserum through a column containing 5 mL of the swelled protein A-agarose gel. By monitoring the absorbance at 280 nm in the column effluent, the nonbound proteins were removed by washing with PBS, and the IgG's were then eluted with acetic acid at pH 2.3 (0.58% acetic acid and 0.15 M NaCl). The fractions containing the IgG's were combined and neutralized; based on the UV absorbance at 280 nm (absorbance/1.4 $=$ mg/mL protein), approximately 33 mg of IgG were isolated from 5 mL of serum, which was then lyophilized and stored at $-20°$ C. The reusable protein A-agarose column was stored in PBS containing 0.02% sodium azide at 4° C.

The protein A-purified IgG was immobilized onto Affigel-10 affinity support. Affigel-10 (5 mL) was washed 3 times with isopropyl alcohol and 3 times with cold distilled water in a Buchner funnel. The gel was then added to a solution of IgG (3 mL in 0.1 M HEPES buffer, pH 7.5) at 4° C. Following 4 hrs of stirring, the gel was precipitated by gentle centrifugation and washed with HEPES buffer (3×3 mL). The remaining active sites on the gel were blocked by resuspending the gel in water (2 mL) and adding ethanolamine HCl (0.5 mL, 1M), and stirring the mixture at 22° C. for 1 hr. The affinity column was useful in adsorbing alachlor and other analytes from aqueous solutions. After binding the alachlor, the column was washed with water (2 mL/min) to remove unbound material and alachlor was eluted with 75% aqueous methanol. This gel affinity column was reusable and was stored in PBS containing 0.02% sodium azide at 4° C.

Results and Discussion. The use of $^{14}C$-labeled haptens allowed facile verification of the covalent attachment of alachlor to the proteins. Through checkerboard assays, the analysis of sera 1.5 months after immunization showed that the rabbits immunized with alachlor-IgG were producing antibodies recognizing the alachlor-BSA screening antigen. The rabbit producing the alachlor antibodies was boosted every 4 to 6 weeks, and bled 10 to 14 days after each boost. Checkerboard and inhibition ELISA assays were conducted to monitor the titre and the affinity of the antibodies in the serum samples. This animal produced the antibodies used throughout the remainder of the discussion. Serum from the seventh bleed was chosen for the development of an inhibition ELISA for alachlor.

During the synthesis of hapten-protein conjugates, alachlor was coupled to IgG using AMSA, and to BSA using AHT. Since only the alachlor portion of these two hapten-protein conjugates were in common, antibodies generated using the alachlor-IgG conjugate and reacting with the alachlor-BSA conjugate were considered to recognize the alachlor moiety and not any portion of the linking reagent nor the protein carrier. The inhibition ELISA demonstrated that the presence of alachlor did in fact inhibit the reaction of the antibodies with the alachlor-BSA conjugate, thereby establishing the specificity of the antibodies toward alachlor. Using antisera from bleed seven, the optimized alachlor inhibition ELISA was most effective with samples containing alachlor concentrations in the ranges from 0.2 ppb to 8.0 ppb, with corresponding percentages of absorbances ranging from 80% to 10%. The percentages of absorbances for the 7 alachlor standards were obtained from 20 separate assays conducted on different days and on different plates. The means, standard deviations, and percent coefficients of variability (% C.V.) were calculated and are summarized in Table 1. The % C.V.'s ranged from 4.2% at 0.2 ppb to 18.6% at 8.0 ppb, and reflected experimental errors between assays. The standard curve based on data in Table 1 was constructed by plotting the mean percentages of absorbances versus the logarithm of the alachlor concentration.

TABLE 1

| Alachlor Conc. (ppb) | ELISA % Absorbance MEAN (n = 20) | ELISA STD. DEV. | Coeff. of Variability (% C.V.) |
|---|---|---|---|
| 0.2 | 78.1 | 3.3 | 4.2 |
| 0.5 | 55.3 | 4.6 | 8.3 |
| 1.0 | 37.4 | 3.6 | 9.6 |
| 3.0 | 22.9 | 3.4 | 14.8 |
| 5.0 | 17.7 | 3.0 | 16.9 |
| 8.0 | 11.3 | 2.1 | 18.6 |

The same data were used to calculate the logit function (see above) standard curve. By plotting the logit of the percentages of absorbance versus the logarithm of the alachlor concentration, a line could be fit through the points. These calculations and line-fittings were carried out with speed and efficiency by a computer program.

The alachlor ELISA was developed for determining the concentration of alachlor in environmental samples. Based on previous in-house studies, alachlor is known to be degraded in soil and water to two major metabolites, an oxanilic acid and a sulfonic acid. Since these metabolites can be present in the environmental water samples, their cross-reactivities with the alachlor antibodies were studied. Both of these alachlor analogs showed very little cross-reactivity with the antibodies (less than 2.5%). Using the inhibition ELISA, the percent cross-reactivities of antibodies in the sera from three serum samples (fourth, sixth, and seventh) of the rabbit were measured against alachlor and 23 analogs. Based on 100% cross-reactivity of the antibodies with alachlor, the analogs 2,6-diethylaniline and α-chloro-2',6'-diethylacetanilide produced no reaction with the antibodies, suggesting the importance of the tertiary amide structure during antigen-antibody interaction. Other chloroacetanilide herbicides (acetochlor, butachlor, amidochlor, metolachlor, and propachlor) showed little to no interaction with the antibodies. The low cross-reactivity of acetochlor (10%) with the antibodies in bleed four decreased slightly in the subsequent bleeds. The absence of the chlorine atom in norchloroalachlor produced a 22% cross-reactivity, suggesting the importance of the chlorine atom in the interaction with the antibody.

Molecules of alachlor were attached to IgG via thioether bonds in the immunization antigen as shown above. It was therefore not surprising to find that some of the alachlor-analogs showing the greatest cross-reactivity contained a thioether functional group. The greatest cross-reactivity, almost twice that of alachlor, was measured with an analog of alachlor with a methyl sulfide group in place of the chlorine (188%); however, when the sulfur was further oxidized as in the sulfoxide analog and sulfone analog, the cross-reactivities were reduced to 15% and 9%, respectively. The 2'-hydroxyethylsulfone analog of alachlor, and the secondary amide methyl sulfide analog of α-chloro-2',6'-diethylacetanilide produced no cross-reactivity. A mercapturate analog, having the formula

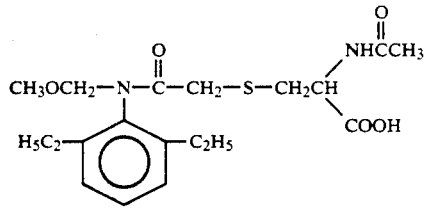

reacted significantly and this result was shown to increase from 18% in bleed four to 65% in bleed seven. The elimination of the anionic charge in the corresponding methyl ester enhanced the reaction to 89.7%. Again, oxidation of the sulfur in the above mercapturate to produce the S=O derivative or conversion of the tertiary amide to the secondary amide mercapturate significantly reduced or eliminated the interaction with the antibodies. The thioacetic acid and glutathione conjugates of alachlor produced 57.0% and 27.5% reaction, respectively.

These cross-reactivity studies established the important functional groups in the structure of alachlor which contribute to its interaction with the antibodies. Minor modifications in the N-methoxymethyl-N-(2,6-diethylphenyl)acetamide portion of alachlor led to significant reductions in reactivity. The presence of either sulfur or chlorine at the carbon-2 of the alachlor molecule was important for the reactivity; however, the opposite effect was observed when the sulfur atom in the thioether analogs was oxidized. The two major alachlor soil and water metabolites (the oxanilic acid and sulfonic acid analogs) showed little reaction with the antibodies. Therefore they are not expected to interfere with the ELISA analysis of alachlor in environmental samples.

Using the antibodies isolated from the serum of the first bleed of the rabbit, an affinity column for alachlor was constructed to study its utility as an isolation and purification tool. The IgG's in the serum of the rabbit immunized with the alachlor-IgG conjugate were purified with a protein A-agarose column. The purified IgG was then immobilized onto the Affigel-10 support. Alachlor ($^{14}$C-labeled) in aqueous solution was passed through the column with a flow rate of 2 mL/min; the column was washed with water and eluted with 75% aqueous methanol. The radioactivity in the wash and eluent were determined by liquid scintillation counting. The results showed that approximately 70% to 80% of the applied radioactive alachlor became bound by the affinity column with the remainder being eluted in the wash. The capacity of the column was less than 1 μg, and once this level was exceeded, alachlor no longer bound to the column. The recovery of applied radioactivity generally ranged from 80% to 100%. In a second experiment, alachlor (0.5 μg) was dissolved into increasing volumes of water ranging from 1 mL to 100 mL. The column effectively extracted alachlor from solutions of 0.5 μg per 1 mL to 0.5 μ/50 mL (0.5 ppm to 10 ppb); however, at 0.5 (5 ppb), the efficiency of alachlor extraction by the column was reduced by 50%.

To eliminate the possibility of non-specific binding of alachlor to the affinity column, other $^{14}$C-labeled analogs were also studied. These included acetanilide herbicides butachlor, acetochlor, metolachlor, and propachlor and the previously mentioned alachlor metabolites mercapturate and its methyl ester. The affinity column bound butachlor and acetochlor, but not metolachlor, propachlor, or mercapturate. Binding was observed with the methyl ester of the mercapturate.

To determine whether the affinity column would be useful in extracting alachlor from a more complex matrix, similar experiments were conducted with alachlor and analogs spiked into human urine. The results (Table 2) suggested that the affinity column continued to show binding specificity for lachlor despite the urinary matrix.

TABLE 2

| | Extraction of Alachlor and Analogs From Human Urine By An Affinity Column[1] | | | |
|---|---|---|---|---|
| Analyte | Conc. μg/2 mL Urine | % $^{14}$C Wash (H$_2$O) | % $^{14}$C Eluent (75% CH$_3$OH) | % $^{14}$C Total Recovery |
| Alachlor | 0.1 | 20.0 | 123.0 | 143.0 |
| Alachlor | 0.6 | 11.0 | 69.0 | 80.0 |
| Alachlor | 1.4 | 37.0 | 48.0 | 85.0 |
| Acetochlor | 1.0 | 61.0 | 38.0 | 99.0 |
| Propachlor | 1.2 | 88.0 | 11.0 | 99.0 |
| Phenol | 0.6 | 95.0 | 4.0 | 99.0 |

[1]Radiolabeled $^{14}$C-analytes were spiked into human urine. The affinity column was prepared from the serum of the first bleed of the rabbit immunized with the alachlor-IgG conjugate.

In a final experiment, the urine from a rat orally dosed with $^{14}$C-alachlor was utilized. Analysis by high performance liquid chromatography with radioactivity detection (HPLC/RAD) showed that the rat urine was devoid of alachlor, but contained 4.5 μg of a mixture of about a dozen metabolites. This urine was spiked with 0.5 μg of radiolabeled alachlor, and the mixture passed through the affinity column.

TABLE 3

Extraction of Alachlor From Rat Urine Containing Alachlor Metabolites By An Affinity Column

| Analyte | Conc. µg/2 mL Urine | % $^{14}$C Wash (H$_2$O) | % $^{14}$C Eluent (75% CH$_3$OH) | % $^{14}$C Total Recovery |
|---|---|---|---|---|
| Alachlor | 0.5 | 14.7 | 83.3 | 97.9 |
| Urine (Rat) | 4.5 | 102.6 | 9.0 | 111.6 |
| Urine + Alachlor | 5.0 | 78.4 | 29.5 | 107.8 |

The results (Table 3) showed that when urine alone was passed through the column, very little radioactivity was extracted, but with alachlor-spiked urine about 30% of the radioactivity was bound by the column. HPLC analysis of the affinity column methanol eluent showed only alachlor; the column wash contained all the alachlormetabolites with low levels of unextracted alachlor. This result again demonstrated the specificity of the antibodies for alachlor even in the presence of closely-related animal metabolites.

The results of the above experiments demonstrated that polyclonal antibodies directed toward alachlor were successfully generated in the rabbits by using the alachlor-IgG conjugate as the immunization antigen. These antibodies were specific toward alachlor and were employed in developing an ELISA assay, which showed a calibration range between 0.2 to 8.0 ppb of alachlor in water with the corresponding percent coefficients of variability ranging from 4% to 19%. The antibodies showed little interaction with the two major soil and water metabolites of alachlor, but did show strong interaction with the sulfide analog which could potentially be produced at low levels during soil and water metabolism of alachlor. Whether this would pose a problem in the ELISA analysis of alachlor in environmental samples is not known. Some of the animal metabolites of alachlor also showed significant interaction with the antibodies. Since the amount of these metabolites in the environment will be low or none, interference with the ELISA analysis of alachlor by these metabolites is not expected. The antibodies were also useful in preparing an affinity column, which showed potential as an isolation and purification tool for alachlor from water and urine.

Example 2

The above experiments indicated that the alachlor ELISA method might be useful for screening samples of natural waters for the presence of alachlor. To evaluate this proposed use, a number of environmental water samples were analyzed independently by the ELISA procedure and by an established GC/MS method. These samples included several hundred river water samples that were collected from a number of sites in the midwest and eastern United States during spring and summer months. Water samples that were intentionally fortified with known amounts of alachlor were also included as controls.

The ELISA analysis predicted that about 80% would contain less than 3 ng/g of alachlor; 99.7% of these predictions were confirmed by the instrumental method. However, among the samples predicted by ELISA to contain 3 ng/g or more alachlor, only 46.2% were confirmed at these levels. Many of these were the intentionally fortified samples. Inspection of the data using different threshold criteria consistently demonstrated that the ELISA method predicted negative samples very accurately, but only 30 to 50% of the positive samples actually contained alachlor above the chosen threshold.

Attempts to correlate this phenomenon with the presence of other pesticides, metal salts, particulates, or other potential mechanisms failed to identify the nature of the interferant. When Tris buffer was substituted for phosphate buffer and Tween 20 and non-fat dry milk were incorporated into the serum and GAR-HRP diluents, the level of interference was substantially reduced in many cases, but not completely eliminated. Further modification of the procedure to include an extraction of the alachlor into organic solvent such as methylene chloride prior to analysis essentially eliminated the occurrence of false positive ELISA results when selected samples were reanalyzed.

Overall, the results from this study demonstrated that the alachlor ELISA method could be applied to natural water samples to select those with a likelihood of containing alachlor for further analysis. This would accomplish a substantial time savings since only a small portion of the total samples, other than the fortified controls, were selected by the immunoassay. Less than 0.5% of the samples which contained alachlor were missed by this strategy at any of the thresholds tested. However, a second analysis was required to confirm that alachlor was present in the positive samples. If a large number of samples were selected by the initial immunoassay, extraction of those water samples with organic solvent and reanalysis by ELISA could be used to further refine the selection process.

Example 3

The generation of antibodies toward butachlor (2-chloro-2',6'-diethyl-N-(butoxymethyl)acetanilide), amidochlor (2-chloro-2',6'-diethyl-N-acetamidomethyl acetanilide), and metolachlor (2-chloro-2'-ethyl-6'-methyl-N-(2-methoxy-1-methylethyl)acetanilide) were accomplished following identical procedures as those described for alachlor. The individual 14C-labeled chloroacetanilide was covalently bound to HSA (human serum albumin) with AHT, and to sheep IgG with AMSA. Calculations showed that 11 to 31 moles of hapten (butachlor, amidochlor, or metolachlor) were conjugated per mole of protein (HSA or IgG).

The hapten-IgG conjugates were used to immunize rabbits. The corresponding hapten-BSA conjugates were then utilized in checkerboard assays to determine the presence of desired antibodies in the antisera. An inhibition ELISA for butachlor was set up with antiserum, butachlor-HSA screening antigen, and butachlor. Similar assays were also set up for amidochlor and metolachlor. In all inhibition ELISA assays, the reaction of the antibodies with the screening antigen was inhibited by the presence of the free hapten; therefore, demonstrating the presence of antibodies in the antisera that were specific to the free hapten.

The sensitivity of the inhibition ELISA for butachlor, amidochlor, and metolachlor was tested with respective standards prepared in DI water. Using the best antiserum, the butachlor ELISA produced an IC50 of 8 ppb. The best antiserum for metolachlor also showed an IC50 of 8 ppb; while the amidochlor antiserum showed an IC50 of 2 ppb. the sensitivity of the amidochlor ELISA was further increased by substituting butachlor-HSA for amidochlor-HSA as the screening antigen, under this format the IC50 was measured at 0.2 ppb.

The specificity of the ELISA for butachlor, amidochlor, and metolachlor were tested using standard solutions of alachlor, acetochlor, butachlor, amidochlor, metolachlor, and propachlor at concentrations of 10 and 50 ppb in DI water. At these concentrations, the ELISA assay for butachlor, amidochlor, and metolachlor was each inhibited only by the respective free hapten, and not by any of the other chloroacetanilides.

The results of our studies with alachlor, butachlor, amidochlor, and metolachlor were all very similar. Antibodies to chloroacetanilides can be generated by immunizing rabbits with a thioether conjugate of chloroacetanilide with protein. The antibodies generated from these thioether haptenprotein conjugates showed reactivity toward the free hapten, but not to the other chloroacetanilide herbicides.

The immunodiagnostic assay kit for the assay of α-haloacetamides by the ELISA method in accordance with this invention comprises:

1. The antibody specific to α-haloacetamides,
2. The α-haloacetamide-protein conjugate immobilized on a solid phase,
3. An anti-immunoglobulin enzyme-labeled reagent which recognizes and reacts with said antibody, and means for terminating and measuring the activity of the enzyme in the system; e.g., dilute $H_2SO_4$ or carbonate and glycine terminating buffers and colorometric measurement,
4. A standard containing a known amount of the appropriate o-haloacetamide,
5. A buffer for dilution of reagents in the test fluid, and
6. Substrate solution for enzyme in solution 3.

The assay kit is preferably used in the following manner:

Reagent 1 is diluted with reagent 5 and allowed to react with reagent 4 (or a sample) at room temperature, this mixture is then added to reagent 2. The solid carrier in reagent 2 is then washed with 5, and reagent 3 is added. The solid carrier in reagent 2 is washed again with 5 and reagent 6 added. The appearance of color is monitored. By comparing the color intensity in the sample and standard, an estimate of the concentration of the α-haloacetamide is obtained.

While the novel immunoassay system according to this invention has been particularly exemplified with respect to prominent commercial herbicides, as described in the above examples, representative of the α-haloacetamides class, it is specifically within the purview of this invention to use the same immunoassay system modified as necessary with regard to conjugate formation, macromolecular carriers, and other starting materials and reagents according to the abilities of those skilled in the art to detect other α-haloacetamides, e.g, allidochlor, metazachlor, pretilochlor, propachlor, and the like.

We claim:

1. Antibodies against haptens conjugated to a protein carrier through the halogen site of the acetyl group of said hapten wherein said haptens are α-chloroacetanilides having the formula

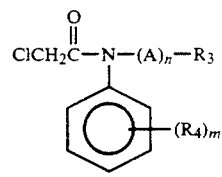

wherein A is a $C_{1-4}$ straight or branched-chain alkylenyl radical and n is zero or 1;

$R_3$ is hydrogen, $C_{1-5}$ alkyl or halo-alkyl; $C_{1-6}$ acyl or acylamido; a heterocycl or heterocyclyl-methyl radical having up to 10 ring atoms of which 1-3 may be nitrogen, oxygen and/or sulfur, optionally substituted with $C_{1-5}$ alkyl or alkoxy radicals; or an —$OR_5$ radical where $R_5$ is a $C_{1-6}$ alkyl, haloalkyl or alkoxyalkyl radical, and $R_4$ is a $R_5$ radical, $CF_3$, $NO_2$ or an alkoxy radical having up to 5 carbon atoms and m is 0-5.

2. Antibodies according to claim 1 wherein said α-chloroacetanilide is acetochlor, alachlor, allidochlor, amidochlor, butachlor, metazachlor, metalachlor, pretilachlor or propachlor.

3. Antigen for raising antibodies against haptens as defined in either of claims 1 or 2 comprising a conjugate of said hapten covalently bound with a protein carrier through the halogen site of the acetyl group of said hapten.

4. Antigen according to claim 3 wherein said carrier is a serum protein.

5. Antigen according to claim 4 wherein said protein is BSA, OA, HSA, IgG or KLH.

6. Antigen according to claim 5 having the formula

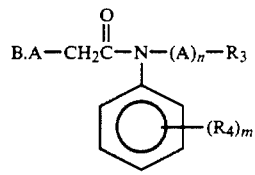

wherein in the moiety —$(A)_n$—, A is $C_{1-4}$ straight or branched-chain alkylenyl radical and n is zero or 1;

$R_3$ is hydrogen, $C_{1-5}$ alkyl or haloalkyl; $C_{1-6}$ acyl or acylamido; a heterocycyl or heterocyclylmethyl radical having up to 10 ring atoms of which 1-3 may be nitrogen, oxygen and/or sulfur, optionally substituted with $C_{1-5}$ alkyl, or alkoxy radicals; or an —$OR_5$ radical where $R_5$ is a $C_{1-6}$ alkyl, haloalkyl or alkoxyalkyl radical, and $R_4$ is a $R_5$ radical, $CF_3$, $NO_2$ or an alkoxy radical having up to 5 carbon atoms and m is 0-5

A is a the residue of a thiolating agent and B is a serum protein covalently bound to A through the halogen site of the acetyl group of said hapten.

7. Antigen according to claim 6 wherein in the moiety B.A—, B is BSA or IgG and A is one of the thioether groups

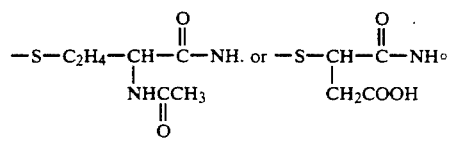

8. Antigen according to claim 7 which is a covalently-bonded conjugate of alachlor and BSA having the formula

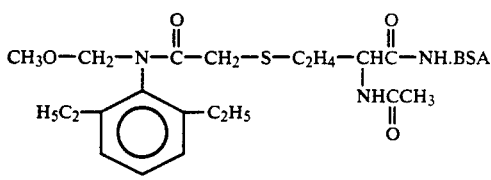

9. Antigen according to claim 7 which is a covalently-bonded conjugate of alachlor and sheep IgG having the formula

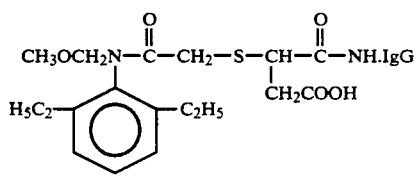

10. Antigen according to claim 7 wherein said hapten is metolachlor.

11. An immunochemical method for detecting and measuring the amount of α-chloroacetanilides having the formula

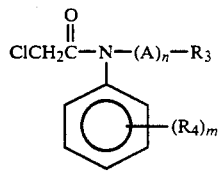

wherein A is a $C_{1-4}$ straight or branched-chain alkylenyl radical;

$R_3$ is hydrogen, $C_{1-5}$ alkyl or haloalkyl; $C_{1-6}$ acyl or acylamido; a heterocycyl or heterocyclylmethyl radical having up to 10 ring atoms of which 1-3 may be nitrogen, oxygen and/or sulfur, optionally substituted with $C_{1-5}$ alkyl or alkoxy radicals; or an $-OR_5$ radical where $R_5$ is a $C_{1-6}$ alkyl, haloalkyl or alkoxyalkyl radical;

$R_4$ is a $R_5$ radical, $CF_3$, $NO_2$ or an alkoxy radical having up to 5 carbon atoms;

m is 0-5 and n is zero or 1, which comprises contacting a test sample, with an antibody of claim 2 using a solid phase colorimetric analysis system in order to detect and measure any of said α-chloro-acetanilides by means of ELISA.

12. Method according to claim 11 wherein said α-chloroacetanilide is acetochlor, alachlor, allidochlor, amidochlor, butachlor, metazachlor, metolachlor, pretilachlor or propachlor.

13. Method according to claim 12 wherein said α-chloroacetanilide is alachlor.

14. Method according to claim 12 wherein said α-chloroacetanilide is metolachlor.

15. Method according to claim 11 wherein said α-chloroacetanilide is acetochlor.

16. An assay kit for the immunochemical analysis of samples potentially containing at least one α-chloroacetanilide as defined in claim 11 by the ELISA method which comprises
  1. The antibody specific to said α-chloroacetanilide,
  2. The conjugate comprising said α-chloroacetanilide covalently bonded to a protein carrier through the halogen site of the acetyl group of the α-chloroacetanilide immobilized on a solid phase.
  3. An anti-immunoglobulin enzyme-labeled reagent which recognizes and reacts with said antibody, and means for terminating and measuring the activity of the enzyme in the system,
  4. A standard containing a known amount of the appropriate α-chloroacetanilide,
  5. A buffer for dilution of reagents in the test fluid, and
  6. Substrate solution for enzyme in solution 3.

17. Kit according to claim 16 wherein said α-chloroacetanilide is selected from the group consisting of alachlor, butachlor, acetochlor metazachlor amidochlor, metolachlor, pretilachlor and propachlor.

18. Kit according to claim 17 wherein said α-chloroacetanilide is alachlor.

19. Kit according to claim 17 wherein said α-chloroacetanilide is acetochlor.

20. Kit according to claim 17 wherein said α-chloroacetanilide is metolachlor.

* * * * *